(12) United States Patent
Gibson et al.

(10) Patent No.: US 7,711,088 B2
(45) Date of Patent: May 4, 2010

(54) METHOD AND SYSTEM FOR X-RAY DIFFRACTION MEASUREMENTS USING AN ALIGNED SOURCE AND DETECTOR ROTATING AROUND A SAMPLE SURFACE

(75) Inventors: David M. Gibson, Voorheesville, NY (US); Walter M. Gibson, Voorheesville, NY (US); Huapeng Huang, Latham, NY (US); Jodi Lynn Reeves, Schenectady, NY (US)

(73) Assignees: X-Ray Optical Systems, Inc., East Greenbush, NY (US); Superpower, Inc., Schenectady, NY (US)

( * ) Notice: Subject to any disclaimer, the term of this patent is extended or adjusted under 35 U.S.C. 154(b) by 0 days.

(21) Appl. No.: 10/893,511

(22) Filed: Jul. 16, 2004

(65) Prior Publication Data

US 2005/0018809 A1    Jan. 27, 2005

Related U.S. Application Data

(60) Provisional application No. 60/489,047, filed on Jul. 22, 2003.

(51) Int. Cl.
*G01N 23/20*    (2006.01)
*G21K 1/06*    (2006.01)

(52) U.S. Cl. .......................................... 378/71; 378/74
(58) Field of Classification Search .............. 378/70–82
See application file for complete search history.

(56) References Cited

U.S. PATENT DOCUMENTS 3,218,458 A * 11/1965 Furnas, Jr. ................... 378/80

(Continued)

FOREIGN PATENT DOCUMENTS

WO    WO 00/58718 A1    10/2000

(Continued)

OTHER PUBLICATIONS

E. D. Specht et al., Uniform texture in meter-long YBa2Cu3O7 tape, Nov. 1, 2002, Physica C, vol. 382, p. 342-348.*

(Continued)

*Primary Examiner*—Edward J Glick
*Assistant Examiner*—John M Corbett
(74) *Attorney, Agent, or Firm*—Jeffrey R. Klembczyk, Esq.; Kevin P. Radigan, Esq.; Heslin Rothenberg Farley & Mesiti P.C.

(57) ABSTRACT

An x-ray diffraction measurement apparatus for measuring a sample, having an x-ray source and detector coupled together in a combination for coordinated rotation around the sample, such that x-ray diffraction data can be taken at multiple phi angles. The apparatus may provide a pole figure representation of crystal orientation of the sample, wherein the pole figure represents the crystal alignment, and a full width half maximum value is calculated from the pole figure for crystal alignment quantification. Data may be taken at discrete positions along a length of the sample, and the sample is in a fixed position during measuring; or data may be taken continuously along a length of the article, as the sample continuously moves along its length in a movement path between the source and detector. The sample may be in the form of a tape, linearly passing through a measurement zone.

9 Claims, 7 Drawing Sheets

U.S. PATENT DOCUMENTS

| | | | | |
|---|---|---|---|---|
| 3,868,506 | A | | 2/1975 | Ogiso .......................... 250/278 |
| 4,078,175 | A | | 3/1978 | Fletcher et al. ............. 250/277 |
| 4,649,556 | A | | 3/1987 | Rinik et al. ................... 378/71 |
| 4,715,053 | A | | 12/1987 | Comstock et al. ............. 378/73 |
| 5,046,077 | A | * | 9/1991 | Murayama ................... 378/80 |
| 5,169,685 | A | * | 12/1992 | Woodruff et al. ............ 427/250 |
| 5,426,092 | A | | 6/1995 | Ovshinsky et al. .......... 505/461 |
| 5,470,668 | A | | 11/1995 | Wu et al. ..................... 428/688 |
| 5,739,086 | A | * | 4/1998 | Goyal et al. ................. 505/473 |
| 5,898,020 | A | | 4/1999 | Goyal et al. ................. 505/239 |
| 5,968,877 | A | | 10/1999 | Budai et al. .................. 505/237 |
| 5,982,034 | A | | 11/1999 | Cava et al. ................... 257/741 |
| 6,269,144 | B1 | | 7/2001 | Dube et al. ..................... 378/71 |
| 6,301,330 | B1 | * | 10/2001 | Kurtz et al. .................... 378/71 |
| 6,555,256 | B1 | | 4/2003 | Christen et al. ............. 428/697 |
| 6,665,372 | B2 | | 12/2003 | Bahr et al. ..................... 378/71 |
| 6,784,139 | B1 | * | 8/2004 | Sankar et al. ............... 505/237 |
| 6,882,739 | B2 | * | 4/2005 | Kurtz et al. .................. 382/109 |
| 2001/0043668 | A1 | * | 11/2001 | Hayashi et al. ............... 378/89 |
| 2002/0027972 | A1 | * | 3/2002 | Joy et al. ...................... 378/85 |
| 2003/0012334 | A1 | | 1/2003 | Kurtz et al. ................... 378/73 |
| 2003/0021885 | A1 | | 1/2003 | Shoup et al. |
| 2004/0016401 | A1 | | 1/2004 | Ignatiev et al. |
| 2004/0096587 | A1 | | 5/2004 | Sambasivan et al. ........ 427/378 |
| 2004/0168636 | A1 | * | 9/2004 | Savvides et al. ...... 118/723 CB |
| 2005/0005846 | A1 | * | 1/2005 | Selvamanickam et al. ... 118/718 |
| 2005/0014653 | A1 | | 1/2005 | Reeves et al. |
| 2005/0141667 | A1 | * | 6/2005 | Berti ............................ 378/79 |

FOREIGN PATENT DOCUMENTS

WO        WO 03/060498 A1      7/2003

OTHER PUBLICATIONS

Brewer et al., Quantitative RHEED Analysis of Biaxially-Textured Polycrystalline MGO Films on Amorphous Substrates Grown by Ion Beam-Assisted Deposition, 2000, Material Research Society Symposium Proceedings, vol. 585, pp. 75-81.*

Koncinski et al., ORNL Superconducting Technology Program for Electrical Power Systems, Annual Report for FY 2000, Apr. 2001, ORNL/HTSPC-12.*

White, On-line Texture Diagnostics for coated Conductor Manufacture, Dec. 30, 2002, Final Report for U.S. DOE SBIR Phase I Contract No. DE-FG02-01ER83208 by MicroCoatings Technologies.*

Egly, et al., "YBa2Cu3O7—Deposition on Metal Tape Substrates", EUCAS '99, 4 pages (Mar. 13-17, 1999).

* cited by examiner

METHOD AND SYSTEM FOR X-RAY DIFFRACTION MEASUREMENTS USING AN ALIGNED SOURCE AND DETECTOR ROTATING AROUND A SAMPLE SURFACE

CROSS-REFERENCE TO RELATED APPLICATIONS

This application claims the benefit of U.S. Provisional Application No. 60/489,047, filed Jul. 22, 2003. This Provisional Application is hereby incorporated herein by reference in its entirety.

FIELD OF THE INVENTION

The present invention relates to x-ray analysis of materials. In particular, the present invention relates to x-ray diffraction techniques for analysis of sample surfaces, especially for in-situ measurement of samples during fabrication thereof.

BACKGROUND OF THE INVENTION

X-ray analysis techniques have been some of the most significant developments in twentieth-century science and technology. The use of x-ray diffraction, spectroscopy, imaging, and other x-ray analysis techniques has led to a profound increase in knowledge in virtually all scientific fields.

One existing class of surface analysis is based on diffraction of x-rays directed toward a sample. The diffracted radiation can be measured and various physical properties, including crystalline structure and phase, and surface texture, can be algorithmically determined. These measurements can be used for process monitoring in a wide variety of applications, including the manufacture of semiconductors, pharmaceuticals, specialty metals and coatings, building materials, and other crystalline structures. This measurement and analysis process requires the detection of diffracted x-ray information at multiple locations in reference to the sample. Conventional diffraction systems are large, expensive and prone to reliability problems. Their size, cost, and performance limit their use to off-line "laboratory" settings.

There is a strong drive in the market for applying this technology to in-line process monitoring—allowing real-time process control. This type of in-line or "in-situ" measurement leads to certain practical concerns—such as the need for smaller instruments, and for sample handling and excitation/detection techniques compatible with the surrounding production environment. For example, the sample may be continuously moving past the instrument on a movement path. The technique must be compatible with both the sample movement and the movement path.

SUMMARY OF THE INVENTION

These capabilities are provided by the present invention, which in one aspect is an x-ray diffraction measurement apparatus for measuring a sample, having an x-ray source and detector coupled together in a combination for coordinated rotation around the sample, such that x-ray diffraction data can be taken at multiple phi angles.

The apparatus may provide a pole figure representation of crystal orientation of the sample, wherein the pole figure represents the crystal alignment, and a full width half maximum value is calculated from the pole figure for crystal alignment quantification.

Data may be taken at discrete positions along a length of the sample, and the sample is in a fixed position during measuring; or data may be taken continuously along a length of the article, as the sample continuously moves along its length in a movement path between the source and detector.

The sample may be in the form of a tape or sheet, linearly passing through a measurement zone between the source and detector.

The apparatus may include a polycapillary x-ray optic for directing a parallel x-ray beam toward the sample from the source.

The apparatus may include a substantially u-shaped plate affixed to the source at one arm and the detector at the other arm; a vertical post supporting the sample; and a base plate under the sample and rotatable around the post. The u-shaped plate may be affixed to the base plate such that it rotatably suspends the source and detector about the sample area.

The present invention also extends to the methods of rotatably mounting a source/detector combination about a sample, to provide an in-situ, process-compatible diffraction measurement technique.

BRIEF DESCRIPTION OF THE DRAWING

The subject matter regarded as the invention is particularly pointed out and distinctly claimed at the conclusion of the specification. The foregoing and other objects, features, and advantages of the invention are apparent from the following detailed description, taken with the accompanying drawings in which:

The use of the same reference symbols in different drawings indicates similar or identical items.

DESCRIPTION OF THE PREFERRED EMBODIMENT(S)

Figure 1:
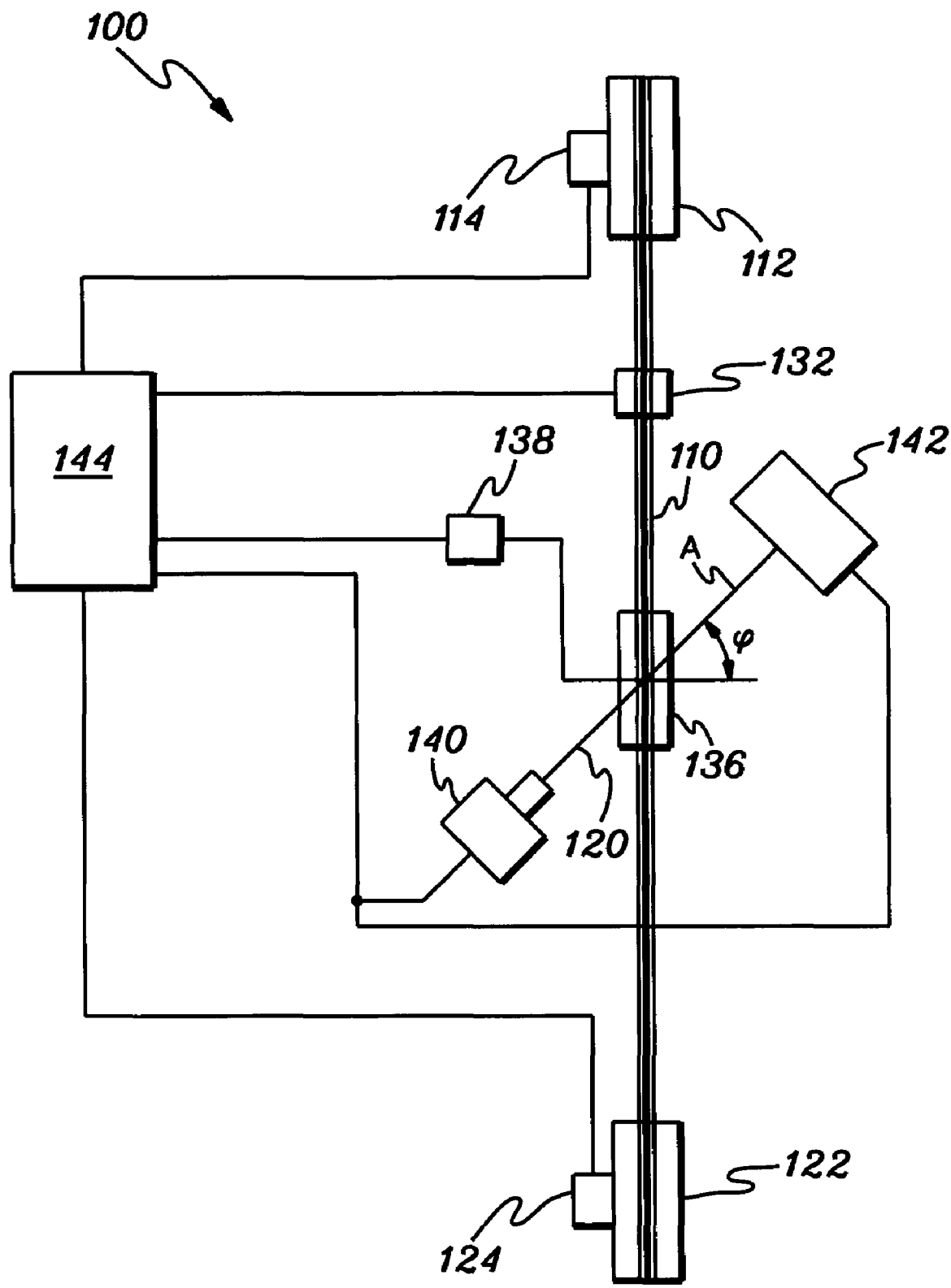
FIG. 1 shows a block diagram of an XRD system for determining the crystallographic texture of a reel-to-reel spool-fed continuous tape.

FIG. 1 shows an XRD system 100 for determining the crystallographic texture of a reel-to-reel spool-fed continuous sample 110.

In this example, the sample is a tape-like configuration, having a high aspect ratio over the sample area. For example, in a superconducting tape embodiment of the present invention as disclosed in copending Application entitled "METHODS FOR FORMING SUPERCONDUCTOR ARTICLES AND XRD METHODS FOR CHARACTERIZING SAME" filed o/a 16 Jul. 2003 in the name of Jodi Reeves as Docket# 1014-SP231, Ser. No. 60/487,739, the entirety of which is hereby incorporated herein by reference, the width of the tape is generally on the order of about 0.4-10 cm, and the length of the tape is typically at least about 100 m, most typically greater than about 500 m. Indeed, embodiments of the present invention provide for superconducting tapes that include a substrate having a length on the order of 1 km or above. Accordingly, the substrate may have an aspect ratio that is fairly high, on the order of not less than $10^3$, or even not less than $10^4$. Certain embodiments are longer, having an aspect ratio of $10^5$ and higher. As used herein, the term 'aspect ratio' is used to denote the ratio of the length of the substrate or tape to the next longest dimension, the width of the substrate or tape.

Turning back to FIG. 1, the tape 110 unwinds from a payout spool 112 and winds onto a take-up spool 122 in reel-to-reel fashion, threading through a sample holder 136 and making physical contact with an encoder 132 or a tape location reader. The encoder 132 provides position tracking and also provides a way to monitor the translation rate of the tape 110 as it translates through the XRD system 100. An alternate way to provide position tracking is to use a tape location reader that utilizes a bar code or dot matrix read head to measure and communicate the exact distance along the length of the tape 110 at which measurements are being performed. The tape location reader may additionally provide information identifying the sample.

A motor 114 such as a stepper motor drives the rotation of the payout spool 112 and advances the tape 110 through the XRD system 100 a desirable increment while a motor 124 such as a torque motor drives the rotation of the take-up spool 122 and provides a desirable amount of tension in the tape 110. Further included in the sample holder 136 is a vacuum port with holes machined through the body of the sample holder 136, that are connected to a pump 138, all to optionally hold the sample against the sample holder. Controller 144 provides a control function, as discussed in greater detail below.

In accordance with the present invention, a source 140 and detector 142 are in fixed relation to each other, and rotatably mounted around the sample holder on a fixture (not shown—discussed further below) to cover all necessary analysis (phi) angles of interest on a portion of the tape, while not interfering with the tape's movement path. In this example, the source and detector pair are aligned along axis "A" such that the source 140 that provides a parallel incident beam of x-ray radiation, such as copper K$\alpha$ radiation, onto the tape 110, and detector 142 detects the diffracted x-rays along the same axis.

For characterization of biaxially textured thin layers or films according to embodiments of the present invention, use of an x-ray source/optic combination that generates parallel x-ray incident beams is desirable. In this regard, use of an x-ray source generating a parallel x-ray incident beam advantageously improves the integrity of the data measured through characterization, as compared to techniques which utilize divergent beams for characterization. More specifically, the precise position of the tape as it translates through the characterization zone, most notably, in the z-direction, affects the precision of the x-ray measurement when relying on systems incorporating divergent beams. In contrast, use of a parallel beam minimizes the affect a variance in the actual z-direction location of the tape undergoing characterization. Such parallel beam transmission can be produced by a polycapillary collimating optic/source combinations such as those disclosed in X-Ray Optical Systems, Inc. U.S. Pat. Nos. 5,192,869; 5,175,755; 5,497,008; 5,745,547; 5,570,408; and 5,604,353; U.S. Provisional Applications Ser. Nos. 60/398,968 (filed Jul. 26, 2002 and perfected as PCT Application PCT/US02/38803) and 60/398,965 (filed Jul. 26, 2002 and perfected as PCT Application PCT/US02/38493)—all of which are incorporated by reference herein in their entirety.

The x-ray source 140 and the detector 142 are oriented within the XRD system 100 such that the incident beam impinges upon the tape 110 at a given angle from the surface of the tape and produces a diffracted beam, also at a given angle to the surface of the tape 110. In the case of YSZ (yttria-stabilized zirconia), that angle is typically about 15° (see FIG. 3). Of course, for different materials, the incident and diffracted beam angles may be at different angles, as the particular physical angles are generally material dependent. The XRD system 100 can be used for a variety of sampling materials by setting the incident angle and the detector angle differently. A goniometer (not shown) may be functionally connected to the sample holder 136 and enables movement of the sample holder 136 through a plurality of motions and angles, including rotation through a range of $\phi$-angles in conjunction with the positioning of the payout spool 112 and the take-up spool 122, respectively. Optionally, the system may include a laser-positioning functionality for sample height calibration.

A controller 144 is in communication with the motors; the encoder 132; the pump 138; the x-ray source 140; and the detector 142. The controller 144 mathematically interprets the diffraction patterns created at the detector 142, yielding quantitative information about the texture of the layer of tape 110 subjected to characterization, which may include the substrate itself in the case of a textured substrate. The graphs produced by the controller 144 are coordinated with sample-identifying information as communicated to the controller 144 by the encoder 132. The final output of the controller 144 is in-plane texture (not just intensity) as a function of position along the tape 110, as is described in reference to FIG. 6 and FIG. 7, discussed in more detail below. The controller 144 may be embodied as a system personal computer (PC), data acquisition software, control software such as LabView, and a set of interfacing components.

In operation, the tape 110 is subjected to characterization at XRD system 100 to undergo texture analysis, and most typically, in-plane texture analysis. While the precise form of the embodiment shown in FIG. 1 is readily adaptable for characterization ex-situ, it may be used in-situ as well, discussed in more detail with other embodiments herein.

Further operational details are as follows: The tape 110 is manually threaded from the payout spool 112 through guides on the sample holder 136 and onto the take-up spool 122. The encoder 132 may physically contact the tape 110. The controller 144 next advances the tape 110 through the XRD system 100 by driving the motor 114 and the motor 124, which drive the rotation of the payout spool 112 and the take-up spool 122, respectively. The encoder 132 measures the distance translated by the tape 110 and at a predetermined increment, e.g., every 10 centimeters, as programmed within the controller 144, the controller 144 halts the translation of the tape 110 through the XRD system 100 by disengaging the motors 114 and 124. The controller 144 engages the pump 138, creating a vacuum through the vacuum ports that adheres the tape 110 flatly within the sample holder 136 and maintains the tape 110 at a fixed vertical height. The controller 144 begins the texture analysis by communicating to the x-ray source 140 to emit the incident beam 120, which impinges upon the tape 110 at an appropriate angle, e.g., 15° for YSZ or 16.4° for a YBCO (YBa$_2$Cu$_3$O$_{7-x}$), and produces the diffracted beam, which is collected at the detector 142 and creates a diffraction pattern that is communicated back to the controller 144. Data is collected by the detector 142 for a time interval of, for example, 10 seconds, after which time the controller 144 communicates to the x-ray source 140 to discontinue generation of the incident beam.

The controller 144 then may engage another motor (not shown) controlling the rotation of the source and detector motor 118 through an appropriate $\phi$-angle, e.g., 5°. The controller 144 then communicates to the x-ray source 140 to emit the incident beam, and data is again collected at the detector 142 and communicated to the controller 144 for a similar time interval. The process continues until data has been collected at various phi angles through a range of phi angles. Typically, data is taken at multiple phi angles, usually at least 3, more typically at least 4, and generally within a range of about +/−5 to +/−25 degrees, more typically about +/−8 to +/−15 degrees. In one embodiment, a range of ϕ-angles, e.g., at increments of 5° from −25° to 25°.

Even greater phi angle ranges can be obtained, without interfering with the tape's movement path, in an in-situ embodiment.

The motor 114 and the motor 124 are reengaged by the controller 144 and advance the tape 110 another increment, e.g., 10 cm, through the XRD system 100 and the measurement process is repeated, such that data collected by the controller 144 can be plotted as a function of position along the tape 110. The encoder 132 communicates to the controller 144 position information for the tape 110 that gets paired with the gathered x-ray texture data. Alternatively, the measurements can all be accomplished while the tape is moving, and at multiple phi angles.

The present invention can be used in connection in any application in which diffraction-type measurements are made on a sample surface. One exemplary application is that of high temperature superconductors as discussed herein.

Figure 2:
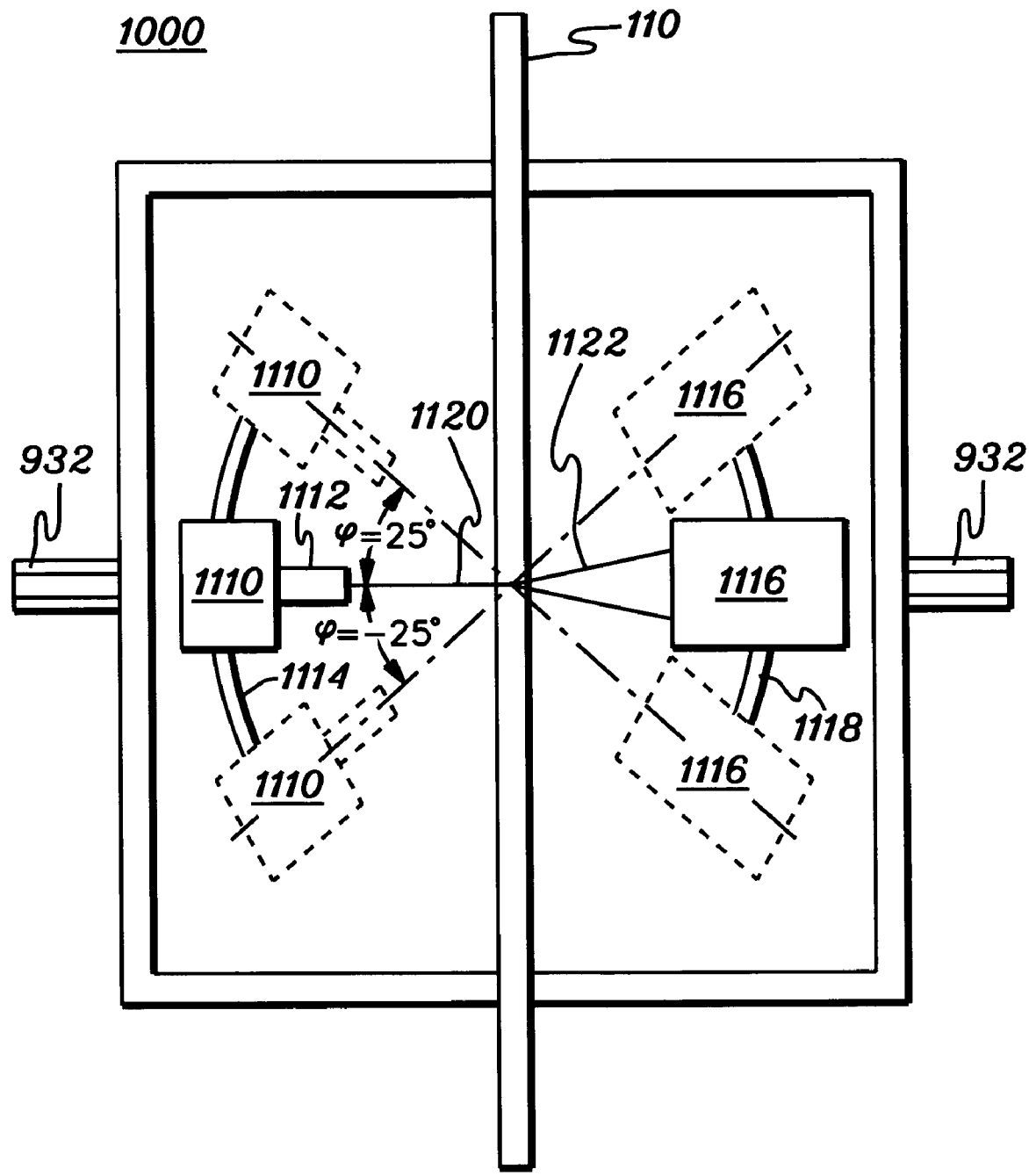
FIG. 2 shows a top view of a translating XRD assembly with a rotatable source and detector.

FIG. 2 shows a top view of an HTS processing apparatus employing the principles disclosed above, notably an XRD system 1000 for determining the crystallographic texture of a reel-to-reel spool-fed continuous tape.

XRD assembly 1000 may also be moveably mounted to a track 932 such that the XRD assembly 1000 itself may translate horizontally through certain in-situ processing sites using its own motor.

Figure 3:
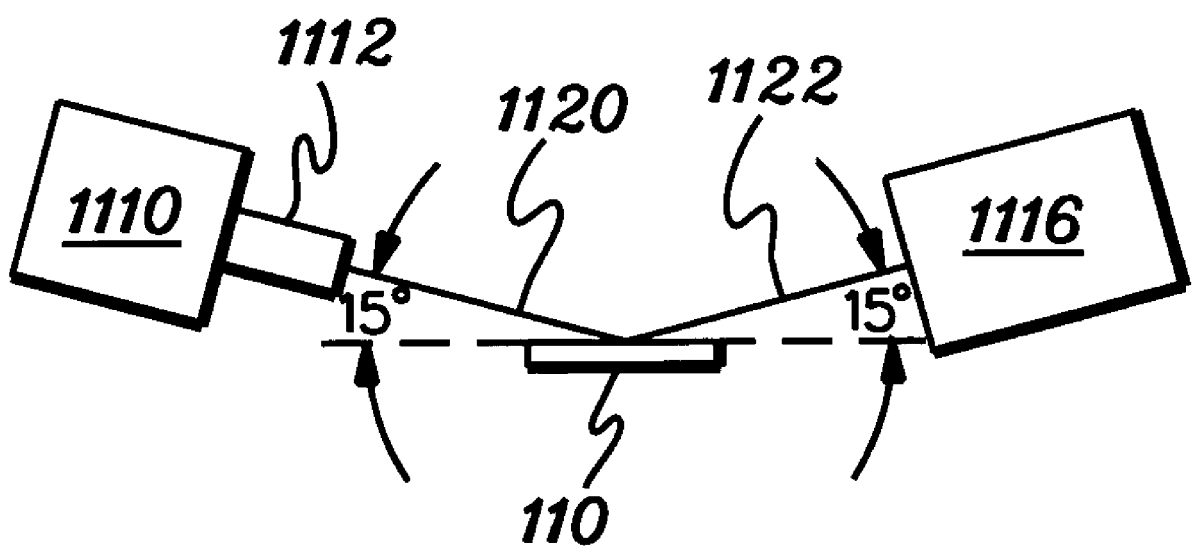
FIG. 3 shows a partial side view of the XRD assembly of FIG. 2.

As shown in detail in FIGS. 2 and 3, the XRD assembly 1000 includes a low-power source 1110 that emits x-ray radiation, which is collimated by an optic 1112 that produces a parallel incident beam 1120 of high intensity, in a similar manner as described above in connection with FIG. 1. The incident beam 1120 interacts with the thin film overlying the tape 110 at an incident angle, which, in the case of YSZ is typically about 15°, to generate a diffracted beam 1122 that is collected at a low-power, high-resolution detector 1116 (e.g., energy sensitive). The source 1110 and the detector 1116 are low power to minimize cooling requirements. The XRD assembly 1000 is vacuum compatible, and thus the source 1110, the optic 1112, and the detector 1116 incorporate the appropriate shielding to prevent contamination and deposited species build-up. The source 1110 may be functionally attached to a track 1114 and the detector 1116 may be functionally attached to a track 1118 such that the motion of the source 1110 and the detector 1116 are coupled together for coupled rotation in ϕ-space. Coupling may be carried out through physical deployment on a single base that rotates along the tracks 1114 and 1118 (or see the embodiment of FIGS. 4 and 5 for a pivoting embodiment of such coupling), or through synchronized coupling electronically. In this regard, the source and detector need not necessarily rotate at the same rate, provided that they are both properly positioned for the targeted phi angle measurement.

In-plane texture of the layer under examination is analyzed via the XRD assembly 1000 as the tape 110 translates through its processing environment, such that the source 1110, the optic 1112, and the detector 1116 are oriented with respect to the tape 110 to perform x-ray diffraction analysis. The optic 1112 collimates x-ray radiation emitted by the source 1110 and produces the parallel incident beam 1120, in contrast to some systems that rely on divergent beams for characterization. As discussed above, the parallel x-ray beam is particularly beneficial for use in systems that have the capability of continuous movement of the tape. In such systems, the parallel beam provides improved process control, as z-axis position of the tape (generally vertical direction) can be difficult to precisely control during continuous movement.

The incident beam 1120 interacts with the thin film deposited atop the tape 110 to produce the diffracted beam 1122, which is collected at the detector 1116 and creates a diffraction pattern that is communicated back to the controller. Data is collected by the detector 1116 for a time interval of, for example, 0.1 to about 20 seconds (typically 0.1 to about 10 seconds, more typically 1 to about 5 seconds), after which time the controller communicates to the source 1110 to discontinue generation of the incident beam 1120. A coupled rotation through a predetermined ϕ-angle next occurs between the source 1110 and the detector 1116 along the tracks 1114 and 1118, respectively. The source 1110 then emits x-ray radiation that is collected as the diffracted beam 1122 at the detector 1116 for a similar time interval, after which time the source 1110 e.g., discontinues emission of x-ray radiation and a coupled rotation through another predetermined ϕ-angle occurs between the source 1110 and the detector 1116 along the tracks 1114 and 1118, respectively. The process continues for a range of phi angles. For example, x-ray diffraction measurements may be performed by the XRD assembly 1000 at phi (ϕ)=0°, ϕ=−10°, and ϕ=+10°, although a range of ϕ-motion is enabled by the assembly between −25° and 25°. At the conclusion of data gathering through the range of ϕ-angles at a particular, the entire assembly itself can be moved to a different part of the process along track 932 if needed. Parameters that may be controlled include tape translation rate (speed), temperature, pressure, gas flow, gas species flow, composition, and combinations thereof.

It is noted that while in the foregoing embodiment, the XRD system typically gathers diffraction data through an area of the tape, as a function of translation rate and sampling duration, the tape could be stopped and discrete points on the tape measured. However, continuous data sampling along an area of the tape during continuous movement may be desirable for processing.

While the foregoing embodiments generally rely on a single source/detector pair for measuring diffraction data at multiple phi angles, the multiple phi angle data can be gathered through alternative structures. For example, multiple detectors, multiple sources, or a combination of multiple sources and detectors can be utilized. In the case of multiple detectors and sources, they may be disposed as shown by the dotted lines in connection with XRD assembly 1000. Alternatively, a single source may be used, to emulate multiple sources. In this case, the source can have incident beams routed to specific phi angles through use of appropriate optics, thereby forming multiple source points from a single source. However the particularities of the source/detector system are embodied, according to one embodiment, it is generally desirable that the system have the capability of multiple phi angle measurement, which enables calculation of pole figures and derivation of FWHM values for superior characterization of the HTS tape under fabrication or under inspection.

Figure 4:
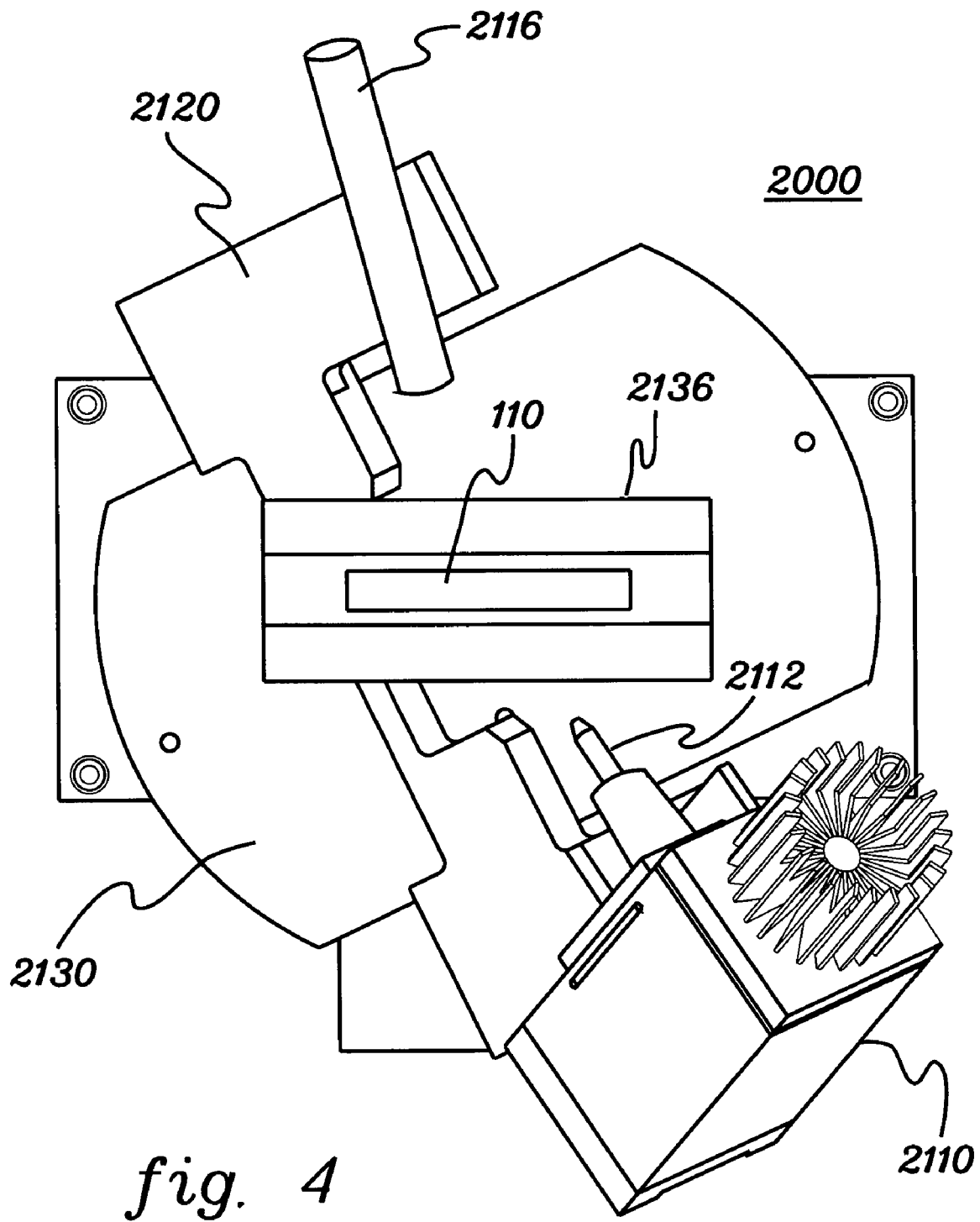
FIG. 4 shows a top, isometric view of another XRD assembly in accordance with the present invention.
Figure 5:
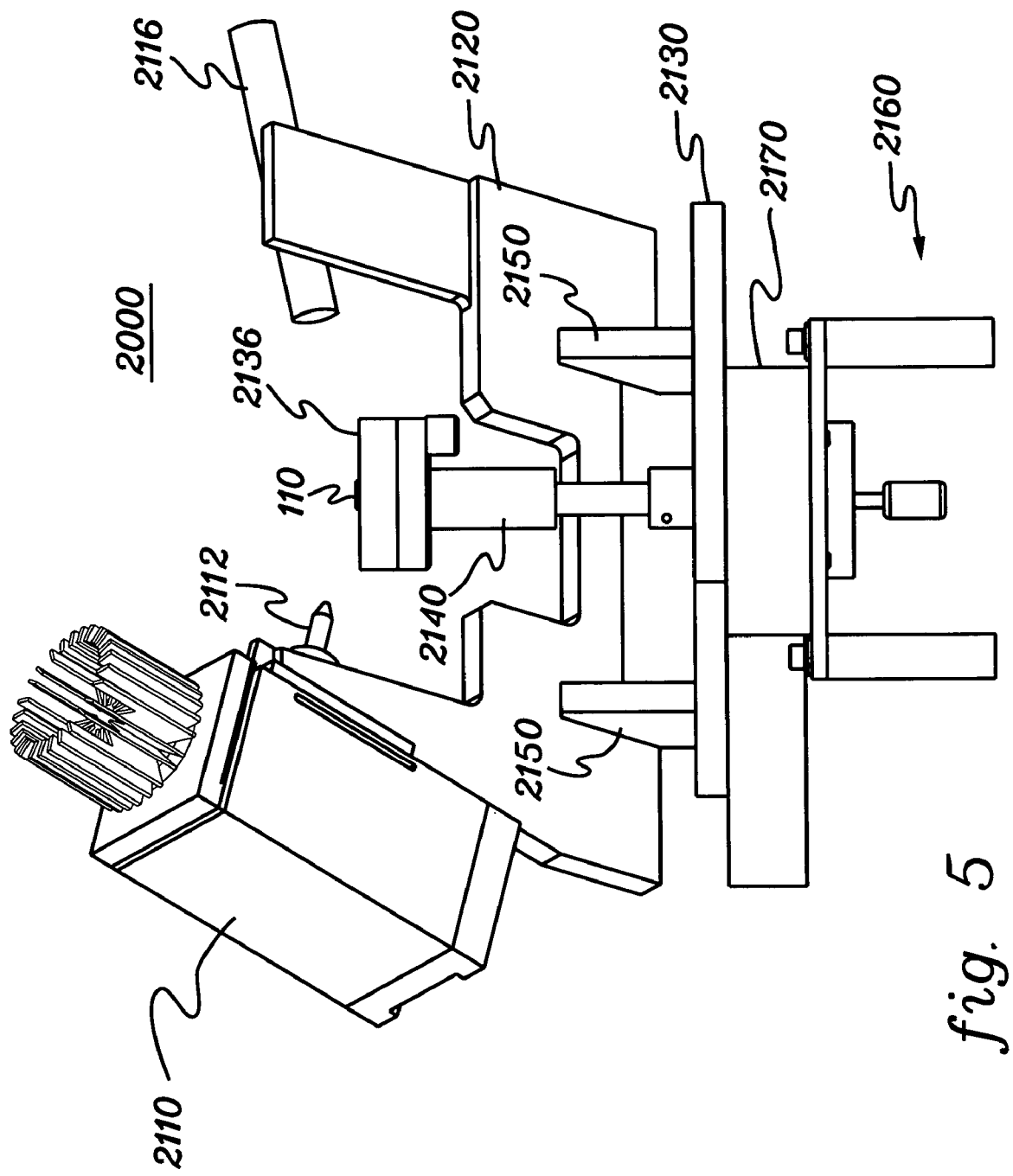
FIG. 5 shows a side, isometric view of the XRD assembly of FIG. 4.

FIG. 4 is a top, isometric view of another XRD assembly 2000 in accordance with the present invention; and FIG. 5 shows a side, isometric view of this XRD assembly. In this embodiment, the source 2110/optic 2112 assembly is known as a low-power X-Beam® source as disclosed in the aboveidentified X-Ray Optical Systems, Inc. US provisional and PCT patent applications. The source 2110 is rigidly mounted to a rigid support structure, e.g., an approximately U-shaped plate 2120 which traverses around and under the sample holder 2136 (forming the tape 110's movement path). Here, the sample holder is fixedly mounted to a stationary post 2140. The detector 2116 is also rigidly mounted to the other end of plate 2120. In one embodiment, the detector is a semiconductor, energy-sensitive detector with a detector area of about 25 mm². Plate 2120 can be fixedly attached to a horizontal, rotating plate 2130 with brackets 2150 such that the source/detector combination can rotate around the sample 110, through the requisite phi angles, but without interfering with the tape's linear movement path in and out of the measurement area. The sample may move continuously through the measurement zone using the actuator principles discussed above, or can be fixed during measurement. Notably in this example, plate 2120 is approximately U-shaped, and fixedly suspends the source/detector combination over the sample 110, and is tilted (somewhat wrapped) around the post 2140 to provide a coordinated, symmetric beam movement through the requisite phi angles. Tilting can also be used to achieve the requisite chi (tilt) angle of about 55 degrees in one embodiment. This movement can be accomplished manually, or using a controllable motor 2170.

The entire assembly can be supported by a base structure 2160.

While the source and detector are shown directly opposed on axis "A" (FIG. 1), they only need to be in some fixed relationship during rotation, not necessarily opposing.

Other improvements to the assembly of FIGS. 4 and 5 are possible. For example, plate 2120 could be hingedly attached to the underlying plate 2130 to provide an additional degree of angular (chi angle) adjustment (either manually or by controllable motor); and the source and/or detector could also be mounted with some adjustment. However, during measurement, these adjustments generally stop, except for the rotational movement of the source/detector combination through the phi angles.

In addition, the entire apparatus could be arranged over a sheet-like material, and provide the same angular rotatability over the area under measurement.

A separate material with differing diffraction characteristics (e.g., silicon wafer slice) could be added to the upper surface of the sample holder (and underneath the sample itself) to suppress background diffraction of other portions of the sample holder. This is especially useful for smaller samples for which the parallel beam may overlap the sample's edges.

Interpretation of Results:

The final output of the controller is in-plane texture as a function of position along the tape 110, as is described below in reference to FIG. 6 and FIG. 7.

Figure 6:
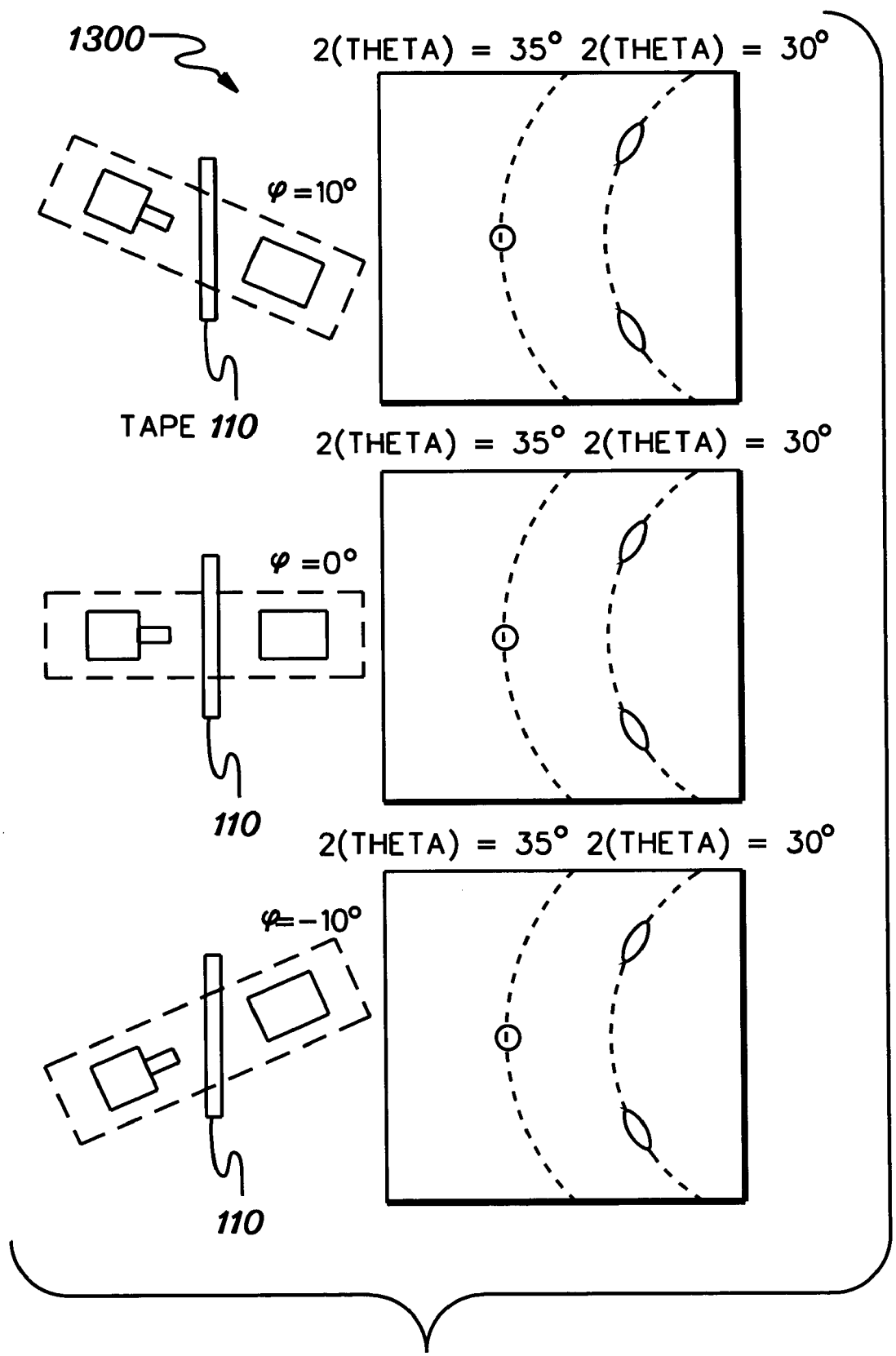
FIG. 6 shows diffraction patterns made by the XRD system at different phi angles.

FIG. 6 shows a plurality of diffraction patterns 1300 that are generated due to the constructive interference in the diffracted beam that occurs when the Bragg equation is satisfied in conjunction with the regularly repeating crystalline structure of the grains within the thin film atop the tape 110. The Bragg equation relates the angles at which X-rays are scattered by planes with an interplanar spacing (d) and states:

$$n\lambda = 2d \sin \theta$$

where n is an integer, $\lambda$ is the wavelength of incident radiation (constant), d is the interplanar spacing, and $\theta$ is the incident angle of the x-ray beam. In satisfying the Bragg equation, diffraction occurs at a specific $\theta$-angle for each unique set of planes within a particular grain. In the case of YSZ, a diffraction signal recorded at $2\theta=32.8°$ corresponds to diffraction from the (111) plane and a diffraction signal recorded $2\theta=34.9°$ corresponds to the (201) plane of YSZ. Of course, such $2\theta$ angles are material specific. With respect to a YBCO superconductor layer a diffraction signal recorded at $2\theta=32.8°$ corresponds to diffraction from the (103) plane and a diffraction signal recorded $2\theta=38.5°$ corresponds to the (005) plane.

Information about the orientation of the individual grains that comprise the layer under study is contained in the diffraction patterns 1300. Each diffraction pattern corresponds to a different $\phi$-angle, and three $\phi$-angles and their corresponding diffraction patterns 1300 are shown in FIG. 6 for illustrative purposes. In practice, it is likely that a diffraction pattern is recorded for each 5° increment between $\phi=-25°$ and $\phi=25°$. As a sidenote, when planes are being described, (001) is used to describe one plane and {001} is used to describe a family of planes. When diffraction directions are being described, [001] denotes a direction and <001> denotes a family of directions. For an XRD system, it is the planes that are doing the diffracting; however, the data in the diffraction pattern is usually described in terms of diffracting directions.

Each constructive interference spot, called a diffraction peak, occurs at a specific location on a specific circle (of varying phi angles) of constant $2\theta$-angle, where different diffracting planes will produce diffraction peaks at different $2\theta$ angles. In the ideal case, in which all grains are perfectly aligned with respect to one another, the diffraction peaks appear as dots. In the worst case, in which all the grains are randomly oriented with respect to one another, the diffraction peaks appear as solid rings that occur along the curves of constant $2\theta$-angle. In the typical case, in which there is a substantial degree of in-plane grain misalignment within the thin film, diffraction peaks appear as elongated spots. In the particular case of YSZ, since the grains of the thin film are grown such that the c axis of their unit cells are approximately parallel to each other, the grains are well aligned in the [001] direction and the diffraction peaks appear as dots along the $2\theta$-angle=35° curve, which corresponds to diffraction by the {001} planes. The diffraction peaks along the $2\theta$-angle=35° curve remain undiminished in intensity as the tape 110 is rotated through the range of $\phi$-angles away from $\phi=0°$ because the c axis of the unit cells does not change relative to the incident beam 210. Further, since there is some degree of in-plane grain misalignment along the [110] direction, the diffraction peaks that occur on the $2\theta$-angle=30° curve, which corresponds to the {111} planes, appear as elongated spots, and diminish in intensity as the tape 110 is rotated through the range of $\phi$-angles away from $\phi=0°$, because the greatest number of grains is aligned along the [110] direction and fewer and fewer grains occur aligned at greater phi angles, as is illustrated in the three diffraction patterns 1300 corresponding to $\phi=10°$, $\phi=0°$, and $\phi=-10°$.

While the (110) plane is the plane of interest to quantify the range of in-plane misalignment that occurs between grains, due to the fact that the [110] direction lies within the plane of the tape 110 and lies parallel to the tape length direction, it is generally difficult to directly obtain diffraction data from the (110) plane. Instead, the {111} set of planes is studied and information, which includes a component that relates information about the {110} set of planes, is extracted.

Figure 7:
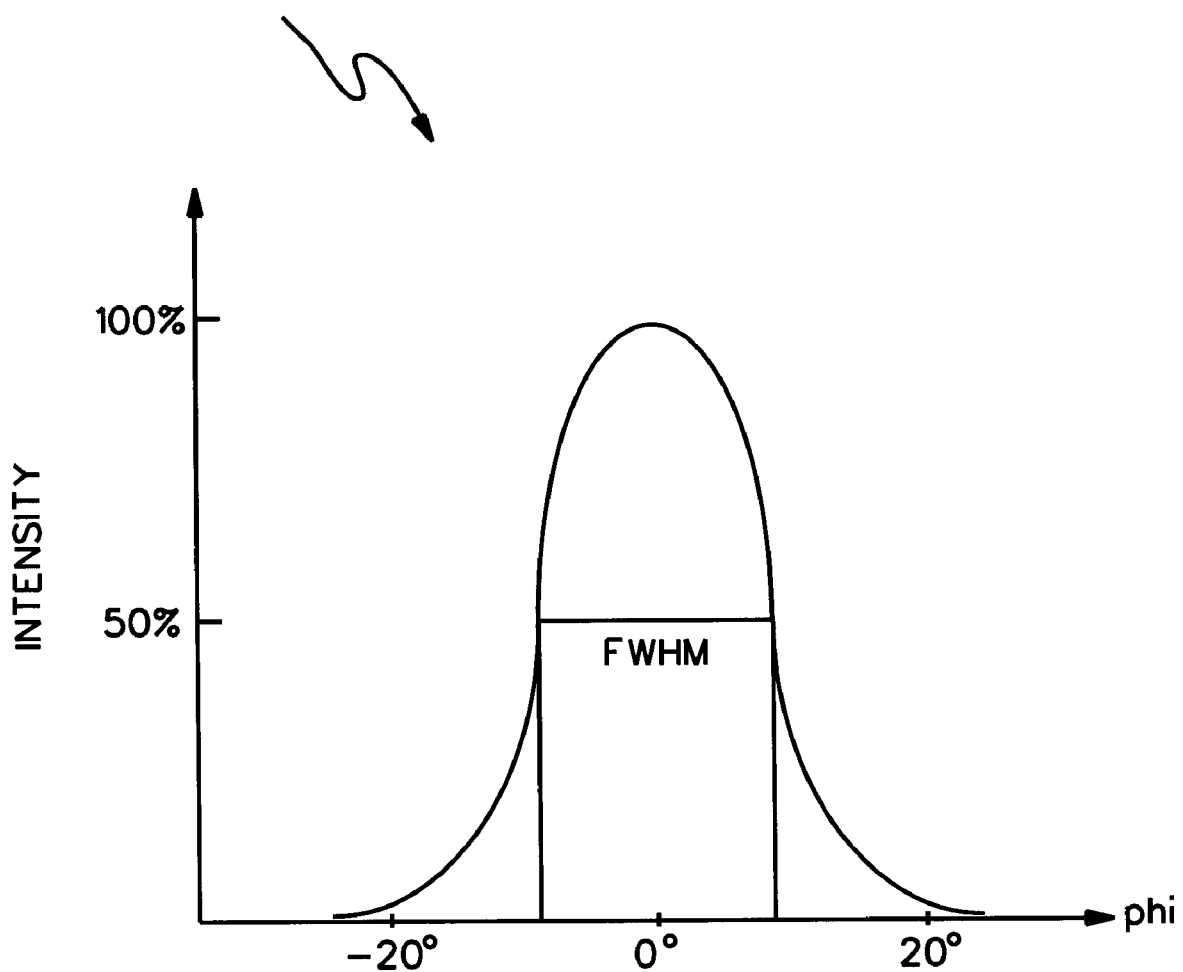
FIG. 7 shows a pole figure plotted based on data gathered by the XRD assembly.

The change in intensity as the tape 110 is rotated in $\phi$ is plotted in FIG. 7, which illustrates a section of a two-dimensional pole figure 1400 that is analyzed to determine the degree of in-plane grain alignment within the thin film atop the tape 110. From the Gaussian that characterizes the pole figure 1400, the full-width at half-max (FWHM) is calculated by the controller. A large FWHM, and hence a broad peak in the pole figure 1400, implies that there is a large range of misorientation in grain alignment along the [110] direction, whereas a small FWHM, and hence a narrow peak in the pole figure 1400, implies a high degree of grain alignment along the [110] direction. According to embodiments of the present invention demonstrating grain alignment, typically, the FWHM spread is less than about 30°, most typically not greater than about 20°. Particular embodiments had a FWHM spread of not greater than about 15°, or even 10°.

In the particular case of YSZ, a spread of 15° in the in-plane texture in the YSZ layer ensures that a spread of less than 10° exists in the in-plane texture in the subsequent epitaxially grown YBCO layer, thus enabling desirable a $J_c$ performance, such as on the order of one million amperes/cm$^2$ in the finished HTS tape.

It is noted that while the foregoing focuses on characterization of a buffer layer formed at one stage of fabrication of an HTS tape, characterization may be carried out on other layers as well, such as on a textured substrate (as in the case of a RABiT substrate), and most notably, on the superconductor (HTS) layer itself.

According to embodiments of the present invention, at least one of the substrate, the buffer layer (more specifically at least one buffer film of the buffer layer), and the superconducting layer has a FWHM not greater than about 25°, preferably not greater than 20°, and more preferably not greater than about 15°, or even about 10°. In this regard, assurance of low FWHM values for the substrate and/or the buffer layer are primarily important of assurance of a low FWHM for the superconductor layer, and the actual crystallographic structure and attendant FWHM for the superconductor layer are of particular significance.

This technique (and its close relatives) may involve irradiating a sample area with any type of high energy radiation, such as x-rays, gamma rays, neutrons or particle beams and observing the resulting diffraction emitted by the sample area. Moreover, these techniques, while optimized in a diffraction measurement, are extendable to any measurement technique (e.g., fluorescence) using the above types of directed radiation.

While superconductor tapes have formed the sample in this application, the principles are extendable to any type of sample media requiring analysis, especially elongated media moving through an in-situ measurement zone.

As noted above, the embodiment disclosed is readily adapted for ex-situ use, it may be incorporated in-situ as well. Likewise, while the embodiment illustrated is particularly adapted for in-situ use (such as in a processing chamber, including IBAD processing chambers and HTS deposition chambers), it may be embodied to be an ex-situ system, such as a tabletop system.

Moreover, in certain industries, the locale of such analyzers may be referred to as "in-line" where the system analyzes substantially all of the material passing through, or "at-line" where samples are readily available from the production line to insert into the analyzer. The disclosed system is readily adaptable for either of these environments.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the following claims.

The invention claimed is:

1. A method of reflective x-ray diffraction measurement of the crystal orientation of a sample, comprising:
    using a low power x-ray source, and detector, rigidly coupled together in a combination for coordinated rotation over the sample;
    using a polycapillary collimating x-ray optic coupled to the x-ray source to produce a parallel x-ray beam on the sample from the x-ray source;
    locating the sample in a sample movement path in and out of which the sample is moveable during measurement;
    taking reflective x-ray diffraction data at multiple, discrete and unique phi angles wherein the detector detects diffracted x-rays from the sample wherein the sample, and the source/detector combination are re-positioned relative to each other at each of said multiple phi angles, whereby said multiple phi angles are defined by a rotation, over a range of at least twenty degrees, about an axis projecting out of a surface of the sample;
    automatically rotating the source/detector combination relative to the sample to automatically achieve the multiple, discrete and unique phi angles;
    providing a pole figure representation. across said multiple phi angles, of said crystal orientation of the sample; and
    taking respective reflective x-ray diffraction data at respective discrete positions of the sample, automatically rotating the source/detector combination relative to the sample to automatically achieve multiple, discrete and unique phi angles at each discrete position, and providing a respective pole figure representation across said multiple phi angles for each discrete position.

2. The method of claim 1, wherein the multiple phi angles comprise at least one angle of at least 25 degrees.

3. The method of claim 1, wherein diffraction data are taken at not fewer than four unique phi angles.

4. The method of claim 1, wherein diffraction data are taken at not greater than twenty phi angles.

5. The method of claim 1, wherein the pole figure represents the crystal alignment, and a full width half maximum value is calculated from the pole figure for crystal alignment quantification.

6. The method of claim 1, wherein said taking is carried out continuously along a length of the article, and the sample continuously moves along said length in the sample movement path between the source and detector during said taking.

7. The method of claim 1, wherein the sample is in the form of a tape or sheet, linearly passing through a measurement zone between the source and detector.

8. The method of claim 7, wherein the sample is at least a portion of a superconducting tape.

9. The method of claim 1, wherein the sample is at least a portion of a superconducting tape.

* * * * *